United States Patent [19]

Huber

[11] 4,400,524

[45] Aug. 23, 1983

[54] GRIGNARD REAGENTS PREPARED FROM 5-HALOPENTAN-2-ONE PROPYLENE KETALS

[75] Inventor: Joel E. Huber, Kalamazoo, Mich.

[73] Assignee: The Upjohn Company, Kalamazoo, Mich.

[21] Appl. No.: 302,004

[22] Filed: Sep. 15, 1981

Related U.S. Application Data

[60] Continuation-in-part of Ser. No. 287,955, Jul. 28, 1981, which is a continuation of Ser. No. 96,646, Nov. 23, 1979, abandoned, which is a division of Ser. No. 11,282, Feb. 12, 1979, abandoned.

[51] Int. Cl.³ .......................................... C07D 319/06
[52] U.S. Cl. ................................. 549/369; 260/397.3; 260/546; 549/456; 562/501; 568/419
[58] Field of Search ...................... 260/340.7; 549/369

[56] References Cited

U.S. PATENT DOCUMENTS 3,413,314 11/1968 Amiard et al. .................. 260/343.2
4,158,012 6/1979 Cooper et al. .................. 260/397.3
4,221,717 9/1980 Chen ............................... 260/340.7

Primary Examiner—Ethel G. Love
Attorney, Agent, or Firm—Sidney B. Williams, Jr.

[57] ABSTRACT

A process for preparing 19-norandrostenedione. Also provides key intermediates of 19-norandrostenedione and methods for preparing them in high yields.

3 Claims, No Drawings

4,400,524

GRIGNARD REAGENTS PREPARED FROM 5-HALOPENTAN-2-ONE PROPYLENE KETALS

CROSS-REFERENCES TO RELATED APPLICATIONS

This application is a continuation-in-part of application Ser. No. 287,955, filed July 28, 1981 pending, which is a continuation of application Ser. No. 096,646, filed Nov. 23, 1979, and now abandoned, which is a division of application Ser. No. 011,282 filed Feb. 12, 1979, and now abandoned.

BACKGROUND OF THE INVENTION

1. Field of Invention

This invention relates to a process for the preparation of 19-norandrostenedione and key intermediates used in said process. 19-norandrostenedione is a 19-nor steroid having the formula I and is shown in the formulae page.

2. Prior Art

Numerous methods of synthesizing 19-nor steroids have appeared in both the steroid literature and patents over the last 20 years.

The use of the Grignard reagent of 5-bromopentan-2-one propylene ketal as the source of five of the six carbons in the A ring of a steroid is described by L. Velluz, et al., Angew. Chem. Internat. Edit., 4, 181 (1965). Other examples of the use of this Grignard reagent and some of the other reaction steps utilized in the process of the invention are described by M. E. Jung, Tetrahedron, 32, 3 (1976). The Grignard reagent is also mentioned in U.S. Pat. No. 3,413,314.

The preparation of ketone via a Grignard reaction on a mixed anhydride has been described by Mukaiyama et al., Chem. Lett. 663, 687 (1974) and Terasawa et al., Tetrahedron, 33, 595 (1977).

Some of the 19-nor steroids of formulae II and III, shown in Formulae page, are known in the art and are used in the process of this invention.

Wherein A is an alkylidene of 2 to 6-carbon atoms or o-phenylene.

Compound III wherein A is ethylene is disclosed in U.S. Pat. No. 3,646,151. Both compounds III and II wherein A is ethylene are described in German Offen. No. 2,449,031 (August, 1976). Compound IIIa is generically disclosed and compound II is generically suggested in U.S. Pat. No. 4,024,166.

The process of preparing 19-norandrostenedione from compound III is disclosed in U.S. Pat. No. 4,024,166. Compounds III and IV wherein A is ethylene are described in U.S. Pat. No. 4,158,012.

BRIEF SUMMARY OF THE INVENTION

The process of this invention can be represented schematically as shown in Chart A.

Wherein R is selected from the group consisting of tertiary alkyl, phenyl, or substituted phenyl, A is the same as defined above, and X is a halogen such as chloro or bromo.

As used herein the term "substituted phenyl" means phenyl substituted by one to three groups selected from hydrogen, alkyl of from 1 to 6 carbon atoms, inclusive; alkoxy of from 1 to 5 carbon atoms, inclusive; bromo, chloro, fluoro, iodo, nitro and dinitro.

Alkylidene of 2 to 6-carbon atoms, inclusive; includes for example, ethylene, 1,3-propylene, 2,3-butylene, 2,2-dimethylpropylene.

The term tertiary alkyl of from 4 to 6 carbon atoms, inclusive; includes for example, t-butyl, 2,2-dimethylbutyl and 2-ethyl-2-methylpropyl.

The term "halo" means bromo and chloro.

DETAILED DESCRIPTION OF THE INVENTION

In step 1 the mixed anhydride V is reacted with the Grignard reagent VI prepared from the ketal IX. The reaction is conducted in the presence or absence of a solvent at temperatures of between 0° and −90° for a period of between 1 and 10 hours. Solvents that can be used include tetrahydrofuran, ethers such as diethyl ether and hydrocarbons such as benzene and toluene. The preferred temperature and reaction time ranges are −30° to −80° C. for 3 to 4 hours, respectively. This is a key step in the process since it provides for the preparation of IV in high yields.

The trione IV may be used in step 2 without separating it from the reaction or it may be used after recovery from the mixture. Conventional methods of recovery such as crystallization, evaporation, chromatography and combinations thereof may be used. It is preferred not to separate trione IV from the mixture for use in step 2.

The mixed anhydride V may be prepared in accordance with Chart B.

Wherein R is the same as defined above. This reaction is conducted in the presence or absence of a solvent and an acid acceptor at a temperature of between 0° and −60° C. for a period of about 0.5 to 3 hours. Solvents that can be used include tetrahydrofuran, diethyl ether, dioxane and toluene. The preferred solvent is tetrahydrofuran. Acid acceptors include trialkyl amines such as triethylamine, triisopropylamine, and heterocyclic amine such as dabco. The preferred acid acceptor is triethylamine. The preferred temperature and reaction time ranges are −20° to −30° C. and 0.5 to 1 hours, respectfully. The starting materials VII and VIII are commercially available or can be prepared by methods well known in the art. For example see U.S. Pat. No. 4,026,729.

The Grignard reagent VI is prepared by reacting 1-halo-4-one propylene ketal with magnesium chips and 1,2-dibromoethane in the presence or absence of a solvent at temperatures of about −20° to +30° C. for a period of about 1 to 24 hours. Solvents that can be used include tetrahydrofuran, tetrahydropyran and mixtures of these ethers with hydrocarbon solvents such as benzene or toluene. The preferred solvent is tetrahydrofuran.

The ketal IX can be prepared from 2-acetylbutyrolactone, a commercially available compound in accordance with Chart C.

Wherein A is an alkylidene of 2 to 6 carbon atoms, inclusive; and HX is a hydrohalic acid, i.e. hydrobromic acid or hydrochloric acid.

In step (a) 2-acetylbutyrolactone is added to an aqueous solution of hydrohalic acid. The conditions for this reaction wherein hydrobromic acid is used has been described in Bacchetti et al., Chem. Abstr. 49, 8288e (1955). The conditions where hydrochloric acid is used are similar to those described by G. W. Cannon et al. Org. Syn. Coll. Vol. IV, 597 (1963).

In step (b) 5-halopentan-2-one is reacted with a glycol under acid conditions in a manner similar to that described by Tschesche et al., Tetrahedron, 33, 735 (1977). In this step it is preferred to utilize 2,2-dimethylpropylene glycol since it yields an enedione III that is solid and therefore easily isolated as a pure product.

In step 2, the trione IV prepared in step 1 is dissolved in a solvent and refluxed with aqueous sodium carbonate for a period of between 1 and 18 hours to yield enedione III. Solvents that can be used include methanol, ethanol, i-propanol and t-butanol. The preferred solvent is methanol. The enedione III can be recovered from the reaction mixture by conventional methods such as evaporation, crystallization, filtration, chromatography and combinations thereof.

In step 3, enedione III is subjected to a reduction to yield the dione II. Methods for conducting this reduction are known in the art. The preferred method is by hydrogenation in the presence of a catalyst such as palladium on carbon.

In step 4, the dione II is dissolved in a solvent and reacted with a strong acid to yield 19-norandrostenedione I. The condition of this reaction and methods of recovering 19-norandrostenedione from the reaction mixture are known in the art.

PREPARATION 1

5-Chloropentan-2-one

The procedure is similar to that described by G. W. Cannon, et al. [Org. Syn. Coll. Vol. IV, 597 (1963)]. A mixture of 150 ml (1.8 mole) concentrated hydrochloric acid and 175 ml water is heated to reflux. To this is added with stirring 107.6 ml (1.0 mole) of 2-acetylbutyrolactone over a 2⅔ hour period. During this time the product is steam distilled from the reaction. After 6 hours total reaction time, approximately 450 ml of distillate is collected. Another 200 ml water is added to the reaction and distillation is continued until no further product in the distillate is detected by tlc carried out on silica gel plates developed in 30 percent ethyl acetate in hexane and visualized with sulfuric acid and ceric sulfate char. The distillate (approximately 500 ml) is extracted with 100 ml of hexane and then the aqueous layer is separated and reextracted with 100 ml of hexane. The two organic layers are washed individually with a single 100 ml portion of water. The combined organic layers are stirred at reflux and dried with the aid of a Dean-Stark trap to yield a hexane solution of 5-chloropentan-2-one.

PREPARATION 2

2-(3-Chloropropyl)-2,5,5-trimethyl-1,3-dioxane

To the hexane solution of 5-chloropentan-2-one prepared in Preparation 1 is added 114.6 g (1.10 mole) of neopentyl glycol. After stirring at reflux for 22 hours, 14.0 (78 percent of theory) of water is collected and tlc is carried out on silica gel plates in 30 percent ethyl acetate in hexane and visualized with sulfuric acid and ceric sulfate char and gc analysis, carried out on a 6 foot, 20 percent SE30 column at 148° indicates that ketalization is complete. The reaction is quenched by the addition of 0.5 ml triethyl amine and then is allowed to cool to 25°. Some unreacted glycol precipitates. The reaction mixture is washed with 150 ml of 2 percent aqueous sodium carbonate, two 100 ml portions of water and finally with 100 ml of 2 percent aqueous sodium bicarbonate. The organic layer is then concentrated at 40° on a roto-evaporator to near constant weight to provide 182.3 g of colorless oil. Simple distillation of this residue gives 162.0 g (78.4 percent chem yield from lactone) of pure 2-(3-chloropropyl)-2,5,5-trimethyl-1,3-dioxane; b.p. 108°/5 mm-111°/3 mm; H nmr (CDCl₃) δ3.45 (m, 6, —CH₂Cl+CH₂—O), 1.91 (m, 4, —CH₂—), 1.36

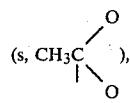

1.03 and 0.87 ppm (s, 6, gem-dimethyl).

PREPARATION 3

Grignard reagent prepared from 5-bromopentan-2-one propylene ketal

The 5-bromopentan-2-one-2,2-dimethylpropylene ketal is prepared by a procedure very similar to that described by R. Tschesche, et al., [Tetrahedron, 33, 735 (1977)]. To 2.92 g of dry magnesium chips slurried in 55 ml of dry tetrahydrofuran at 0° is added 1.5 ml of 1-bromopentan-4-one-2,2-dimethylpropylene ketal as a 89% solution in cyclohexane and the temperature is slowly increased whereupon at 20° 0.1 ml of 1,2-dibromoethane is added. A 14° exotherm is noted. The temperature is adjusted to 22° and the remainder of the 10.0 ml of the bromoketal is added dropwise over 6 minutes. The temperature is maintained between 20° and 26° and after 0.5 hour stirring thin layer chromatograph of an acetone quenched sample shows no remaining bromo ketal. The weight of this gray slurry is about 98 g after being rinsed with additional tetrahydrofuran. A titration for Grignard reagent shows 0.55 m.

PREPARATION 4

Grignard Reagent prepared from 2-(3-chloropropyl)-2,5,5-trimethyl-1,3-dioxane A 2.0 g (82.3 mg atom) sample of magnesium chips is dried overnight at 40° under a dry nitrogen atmosphere. About 70 ml of tetrahydrofuran (freshly distilled from calcium hydride) is added and about 20 ml is removed by distillation at atmospheric pressure. At this point 2 ml of 2-(3-chloropropyl)-2,5,5-trimethyl-1,3-dioxane and 0.40 ml (4.4 mole) of 1,2-dibromoethane are added and after about 20 minutes, stirring at reflux, the Grignard reaction seems to initiate. The remainder of the 12.04 ml (60 mmole) of 2-(3-chloropropyl)-2,5,5-trimethyl-1,3-dioxane is added dropwise over 10 minutes and the slurry is stirred at reflux. Little exotherm is noticed during the Grignard formation. After 1 hour reflux tlc indicates the absence of any remaining 2-(3-chloropropyl)-2,5,5-trimethyl-1,3-dioxane. The gray slurry is allowed to cool and then is filtered in a dry-box into a vial fitted with a serum cap. The salts are washed with about 2 ml of dry tetrahydrofuran and the combined filtrate and wash weighs 58.5 g. Titration for 2-(3-chloropropyl)-2,5,5-trimethyl-1,3-dioxane Grignard reagent shows the solution to be 0.872 m (85 percent chem. yield).

PREPARATION 5

Mixed anhydride V

A 7.15 g (30 mmole) sample of diketo acid is dried at 45° overnight under a dry nitrogen atmosphere. Approximately 80 ml of dry tetrahydrofuran is added and about 10 ml is removed by distillation at atmospheric pressure. These operations were designed to ensure an oxygen and water free solution. The solution is cooled to −38° and 5.02 ml (36 mmole) triethyl amine is added followed by the dropwise addition of 4.19 ml (34 mmole) pivaloyl chloride over 1 minute. A precipitate of triethyl amine hydrochloride forms immediately and after stirring this slurry at about −30° for 20 minutes, the temperature is adjusted to −74°.

PREPARATION 6

Trione IV

To the above slurry is added 45 ml (38 mmole) of the Grignard reagent prepared in Preparation 4 dropwise over 4 hours at −71° to −75°. The reaction is quenched with 100 ml of 3 percent aqueous ammonium chloride with stirring. After extraction with 150 ml and 100 ml portions of methylene chloride the combined organic (lower) layers are washed with 150 ml of water and then concentrated on the evaporator at 40° to give a colorless higher boiling residue consisting mainly of trione IV.

PREPARATION 7

Enedione III

The residue of trione IV prepared in Preparation 6 is taken up in 50 ml of methanol and stirred at gentle reflux under nitrogen for 5 minutes. Then 1.01 ml of saturated aqueous sodium carbonate solution is added and the mixture is stirred at reflux for 16 hours. Tlc shows complete converson of trione IV to enedione III. The reaction is allowed to cool to 25° and is added to 150 ml of water and 10 ml of a saturated sodium chloride solution. This is extracted with two-100 ml portions of methylene chloride and each organic layer is back washed sequentially with 100 ml water. The combined organic layers are concentrated on the roto-evaporator to constant weight to provide 13.70 g of colorless oily III; uv max (EtOH) 248 nm ($\epsilon$=9,270). Using an $\epsilon$ value of 14,470 for pure III, this oil represents a 78 percent chem. yield of III from diketo acid.

PREPARATION 8

Crystallization of III

The crude enedione III from Preparation 7 from 30 mmole run (77 percent yield based on uv) is taken up in 50 ml hexane at 50°. Slow cooling and seeding gives solids which, after stirring at −15° for 15 minutes are collected by filtration. The solids are washed with 50 ml of −15° hexane and dried in vacuo at 45° for 16 hours to provide 7.54 g (67 percent yield from diketo acid) of 1 spot by tlc III; mp 90°–91°. Recrystallization of a sample from 40 percent aqueous methanol gives III as a solid melting at 92°–93.5°; H nmr (CDCl$_3$) δ3.50 (s, 4, —CH$_2$—O), 1.40

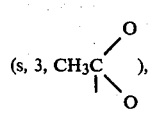
(s, 3, CH$_3$C ), 1.04 (s, 3, C$_{13}$Me) and 0.96 and 0.94 ppm (s, 6, gem-dimethyl); uv max (EtOH) 248 nm ($\epsilon$=14,470).

PREPARATION 9

A 5.50 g aliquot of III from Preparation 7 in 35 ml of methanol containing 200 mg of 5 percent palladium on carbon (50 percent water wet) and 27 mg of potassium hydroxide is hydrogenated at 13°–22° at atmospheric pressure for 112 hours. Tlc indicates the reduction is complete. The catalyst is removed by filtration and washed with methanol.

EXAMPLE 1

19-Norandrostenedione

The crude material of Preparation 9 is stirred at reflux under nitrogen for 5 minutes. Then 1.0 ml of 6 N hydrochloric acid is added and during the subsequent 4 hours stirring period the solution is slowly concentrated by distillation to approximately 25 ml. Tlc indicates the reaction is complete. The temperature is adjusted to 50° and seeded. Solids form slowly and after 15 minutes, 20 ml of aqueous ater is added. The slurry is allowed to stand at 10° for 30 minutes. The solids are collected by filtration, washed with 10 ml of cold 60% water methanol and dried under reduced pressure at 50° overnight to afford 1.99 g of 19-norandrostenedione (61 percent yield from diketo acid), mp 166°–168°.

FORMULAE

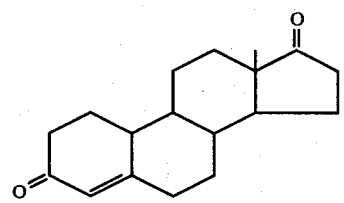
I

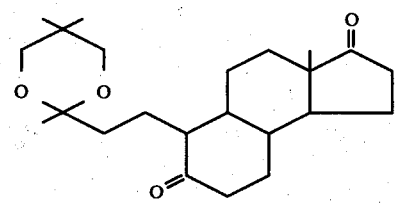
II

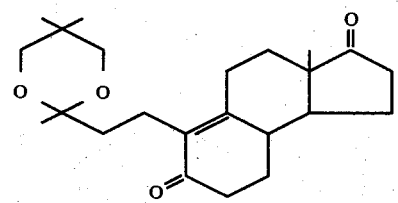
III

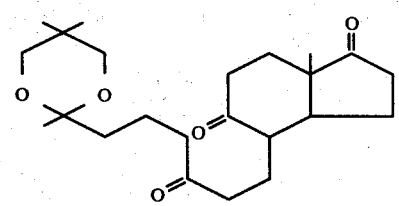
IV

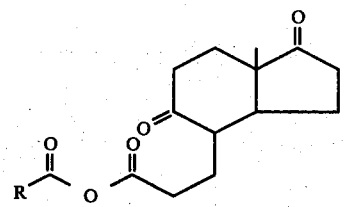
V

-continued
FORMULAE
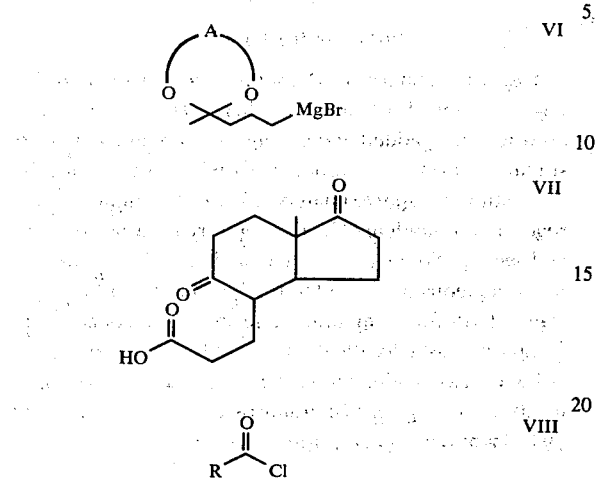
CHART A
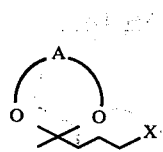
-continued
CHART A
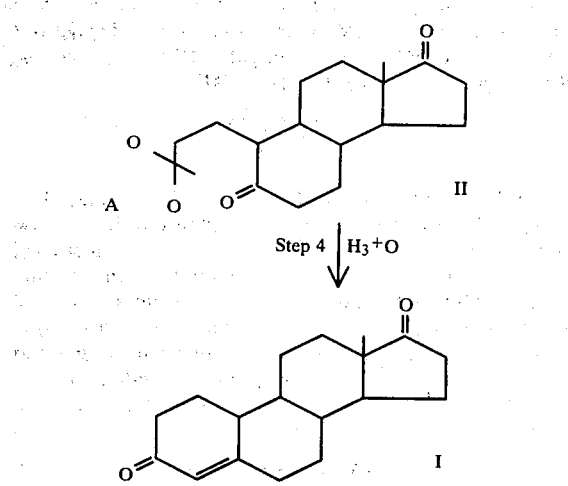
CHART B
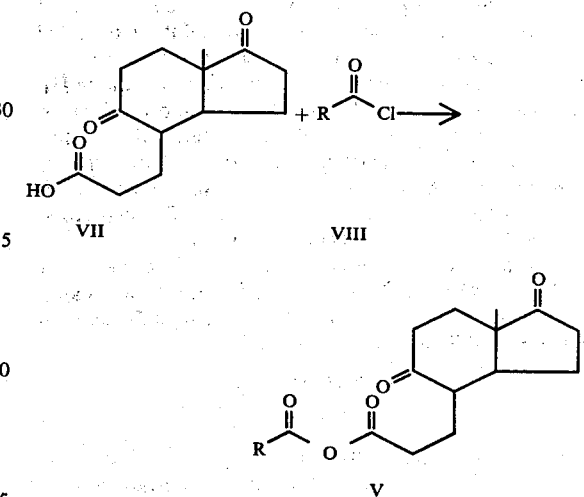
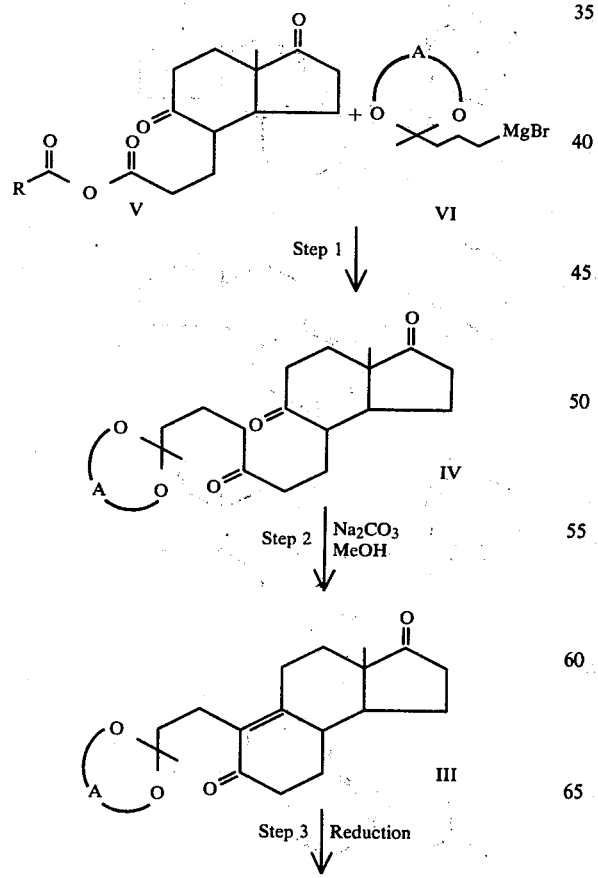
CHART C
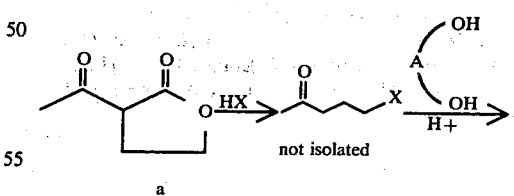
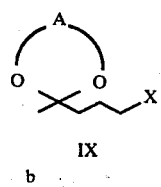
I claim:
1. A compound selected from the group consisting of

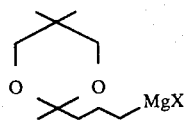

wherein X is selected from the group consisting of bromine and chlorine.

2. A compound of claim 1 wherein x is chlorine so that the specific embodiment is the Grignard reagent prepared from 5-chloropentan-2-one-2,2-dimethylpropylene ketal.

3. A compound of claim 1 wherein X is bromine so that the specific embodiment is the Grignard reagent prepared from 5-bromopentan-2-one-2,2-dimethylpropylene ketal.

* * * * *